United States Patent
Spangenberg et al.

(10) Patent No.: US 7,355,096 B2
(45) Date of Patent: Apr. 8, 2008

(54) RYEGRASS POLLEN-SPECIFIC PROMOTERS AND EXPRESSION CONSTRUCTS

(75) Inventors: German Spangenberg, Bundoora (AU); Angela Jane Lidgett, Kew (AU); Natasha Petrovska, Thomastown (AU)

(73) Assignee: Molecular Plant Breeding Nominees Ltd, Bundoora (AU)

( * ) Notice: Subject to any disclaimer, the term of this patent is extended or adjusted under 35 U.S.C. 154(b) by 0 days.

(21) Appl. No.: 10/561,283

(22) PCT Filed: Jun. 18, 2004

(86) PCT No.: PCT/AU2004/000802

§ 371 (c)(1),
(2), (4) Date: May 3, 2006

(87) PCT Pub. No.: WO2004/113536

PCT Pub. Date: Dec. 29, 2004

(65) Prior Publication Data

US 2006/0282919 A1    Dec. 14, 2006

(30) Foreign Application Priority Data

Jun. 20, 2003   (AU) .............................. 2003903132

(51) Int. Cl.
C12N 15/82    (2006.01)
C12N 5/04     (2006.01)
C12N 5/10     (2006.01)
A01H 5/00     (2006.01)

(52) U.S. Cl. ...................... 800/278; 435/419; 435/468; 536/24.1; 800/287; 800/295

(58) Field of Classification Search ................. None
See application file for complete search history.

(56) References Cited

U.S. PATENT DOCUMENTS 6,180,368 B1 *  1/2001  Singh et al. ................ 435/69.3
2004/0045053 A1 *  3/2004  Greenland et al. .......... 800/284

FOREIGN PATENT DOCUMENTS

WO    WO 93/04174 A1    3/1993

OTHER PUBLICATIONS

Hamilton (1992) Journal Plant Molecular Biology vol. 18, pp. 211-218).*

Hannenhalli et al., (2001) Promoter prediction in the human genome. Bioinformatics 17: S90-S9.*

Hauschild, et al (1998) Isolation and analysis of the gene bbe1 encoding the berberine bridge enzyme from the California poppy *Eschscholzia californica* Plant Molec. Biol. 36:473-478.*

Kim et al., (1994) A 20 nucleotide upstream element is essential for the nopaline synthase (nos) promoter activity. Plant Molecular Biology 24: 105-117.*

(Continued)

*Primary Examiner*—Anne Marie Grunberg
*Assistant Examiner*—Brendan O. Baggot
(74) *Attorney, Agent, or Firm*—Christensen O'Connor Johnson Kindness PLLC

(57) ABSTRACT

The present invention relates to a nucleic acid molecule capable of modifying pollen-specific expression, constructs including the molecule and methods of using the molecule.

21 Claims, 9 Drawing Sheets

```
AGTGTAACCTAGGACTCTAGGCCAGATCGTGACATTGGAATAGTGCACGACATTTCCCTG
CATACGTAACGCCTATGGGTATGGAGCTTCATACCGAGACTCCCAAGTATCATACCAGAG
GGGACGTGGCCTCCTCTATTCTAGGGGCGACGCCACCCCTGGCAATAAAAATAGGAACTT
CTACTAGATAAGGGGGAGGGCTCGAAGCAACAAAGAGGCTAAGAAAGGCGAAAATCAAGC
AAGAACACAAACCCAACAAGCCAGAGCTAAACAAGCCTTAGCACCCATGGTCTCTCGCACT
CGAAAATAACGAGGCGAGATGACACTCTTTCCATTCCAACATTTCATAGCTTAGTAGCTA
CCCAAGAGGAGGAACAAGCACCAGCCAACTTCCCGCCGGAAGCGGCACCCACTCAGACTC
ACTAGCACCTCGCGCACAATCAATAAAAACACCACCACCAAGAAGTAGGGTTGTTATTGA
CGATGTATTCTCGGTCCCTAAATTGTATATCTCTCGTGTGCATGTGGATGTTACCCAATG
GAATCGTGGTCACAAGCCCACCACCTACATAAGAATATACAACCGGGAACCAAAACCCTG
ACACTAGGCAAATCATTAGGGCCACGCCGACTATCTCATTCCCGCACGCGTCTAGGTTTC
CCGCCCGTTTCTACCCCTTGTGGGTATCCCCCATCATTCTTGTTTGTATTGGTCCAAAAA
ATCAGCAAAGTTTGCTTTGCCGTGTGTATTCATATAACACTCGATAATGACCCCATCGGC
CTTATTTTTTATTGTTTCCTTCCTGCCTTTTCTTCCCCGCGATCTTTCAGCCCTTGTGT
CCCTATATATACCCATCTCTCGGATACATAATTCACAACCCACCTCCACCATAAAGTACA
AAGAAGAGCATTCACTCTAGGGAACCTTGAAGGTGTGGGTCTTGTATAAAGTCATGGCAG
CGATGTACAAGGCTTGCATCATCTAGGGTTCCTAGATGAAACGCTTAGCATCAGCTAGGT
AATAATAACCTTGGGTGACATAGTTGCCAAAACAAGCTTATATTGTGCACATGTGCGTGT
GTCATGGGACTGGAAAGGGTCGCCGGTGTGAACCACTGATGTGTGCTGCCATTTAGGAAG
ACTCTAGATGAATGGGGGAACTCCCAGGTCGGGTCCACCAGAGGAAAATCTTGCGAGATC
TTGGGCTGAATCATTGAATTTCATGTACCAAGTAACTAACCAAATAGAAACCAAGAGAAA
ATCTCATTGTTCAGCAGTCTTTCGTTGAATTTTAGAGGGATATGCGGTGGAGGGCCTCCG
AGGCAGCGTTTCGCCGCATACCACATTTCGGAGGGCCGAAATCCATCCAAAACTATCAAG
TGGGACTAACACATGAACATACGTGTGTTGAGATTCTGAGATGCCCAAGAGCCAGCTCCC
GCGCGTGACCCACTTCACCGGCGACCGCTGCCACTTAGGAAGGTTCTTGACTGAAAAAGG
GAAAACTCCCACGATGGGTTCACCCGAGGAAATCTTGCGAGATCATGAGCTCAACCATTG
CTTTCCATGTTCCTATGAACTAACCAAACAATCAAGTGAAAATCCCATTGGCCACCGGTA
GTTTAAATAATTTCAGAAGCGTAGACCATGCTTCGGATGGCCAAAATCCACCTAAAACTT
GCAAGTGGGCCTAATATGTGTAAAAGTGTGCTGGGATGGTAGGGGGCCAAGAGCTAG
CTAGCGTGGCGGCATGCTGTCGTGGGAGTAAGAAAATCTCTGCACAGTGTGTTTTAGGG
```

OTHER PUBLICATIONS

Maiti et al., (1997) Promoter/leader deletion analysis and plant expression vectors with the figwort mosaic virus (FMV) full length transcript (FLt) promoter containing single or double enhancer domains Transgen. Res., 6:143-156, see Fig. 4.*

Doelling et al (1995) The minimal ribosomal RNA gene promoter of *Arabidopsis thaliana* includes a critical element at the transcription initiation site 8 (5) 683-692).*

Dolecek, C., et al., "Molecular Characterization of Phl p II, a Major Timothy Grass (Phleum Pratense) Pollen Allergen," FEBS Letters 335(3):299-304, 1993.

Griffith, I.J., et al., "Cloning and Sequencing of Lol pl, the Major Allergenic Protein of Rye-Grass Pollen," FEBS Letters 279(2):210-215, 1991.

Lu, G.-H., et al., "Induction of Male Sterility by the Integration of Chimeric RTS-Barnase Gene Into Rice (*Oryza sativa* L.) Genome," Acta Phytophysiologica Sinica 26(2):171-176, 2000.

Sidoli, A., et al., "Cloning, Expression, and Immunological Characterization of Recombinant Lolium Perenne Allergen Lol p II," Journal of Biological Chemistry 268(29):21819-21825, 1993.

Zhan, X.-Y., et al., "Nuclear Male Sterility Induced by Pollen-Specific Expression of a Ribonuclease," Sexual Plant Reproduction 9(1):35-43, 1996.

Bhalla, P.L., et al., "Antisense-Mediated Silencing of a Gene Encoding a Major Ryegrass Pollen Allergen," Proceedings of the National Academy of Science USA 96(20):11676-11680, Sep. 1999.

Bhalla, P.L., et al., "Reduction in Allergenicity of Grass Pollen by Genetic Engineering," International Archives of Allergy and Immunology 124(1-3):51-54, Jan.-Mar. 2001.

* cited by examiner

```
AGTGTAACCTAGGACTCTAGGCCAGATCGTGACATTGGAATAGTGCACGACATTTCCCTG
CATACGTAACGCCTATGGGTATGGAGCTTCATACCGAGACTCCCAAGTATCATACCAGAG
GGGACGTGGCCTCCTCTATTCTAGGGGCGACGCCACCCCTGGCAATAAAAATAGGAACTT
CTACTAGATAAGGGGGAGGGCTCGAAGCAACAAAGAGGCTAAGAAAGGCGAAAATCAAGC
AAGAACACAAACCCAACAAGCCAGAGCTAAACAAGCCTTAGCACCATGGTCTCTCGCACT
CGAAAATAACGAGGCGAGATGACACTCTTTCCATTCCAACATTTCATAGCTTAGTAGCTA
CCCAAGAGGAGGAACAAGCACCAGCCAACTTCCGCCGGAAGCGGCACCCACTCAGACTC
ACTAGCACCTCGCGCACAATCAATAAAAACACCACCACCAAGAAGTAGGGTTGTTATTGA
CGATGTATTCTCGGTCCCTAAATTGTATATCTCTCGTGTGCATGTGGATGTTACCCAATG
GAATCGTGGTCACAAGCCCACCACCTACATAAGAATATACAACCGGGAACCAAAACCCTG
ACACTAGGCAAATCATTAGGGCCACGCCGACTATCTCATTCCCGCACGCGTCTAGGTTTC
CCGCCCGTTTCTACCCCTTGTGGGTATCCCCCATCATTCTTGTTTGTATTGGTCCAAAAA
ATCAGCAAAGTTTGCTTTGCCGTGTGTATTCATATAACACTCGATAATGACCCCATCGGC
CTTATTTTTTATTGTTTCCTTCCTGCCTTTTCTTCCCCGCGATCTTTCAGCCCTTGTGT
CCCTATATATACCCATCTCTCGGATACATAATTCACAACCCACCTCCACCATAAAGTACA
AAGAAGAGCATTCACTCTAGGGAACCTTGAAGGTGTGGGTCTTGTATAAAGTCATGGCAG
CGATGTACAAGGCTTGCATCATCTAGGGTTCCTAGATGAAACGCTTAGCATCAGCTAGGT
AATAATAACCTTGGGTGACATAGTTGCCAAAACAAGCTTATATTGTGCACATGTGCGTGT
GTCATGGGACTGGAAAGGGTCGCCGGTGTGAACCACTGATGTGTGCTGCCATTTAGGAAG
ACTCTAGATGAATGGGGGAACTCCCAGGTCGGGTCCACCAGAGGAAAATCTTGCGAGATC
TTGGGCTGAATCATTGAATTTCATGTACCAAGTAACTAACCAAATAGAAACCAAGAGAAA
ATCTCATTGTTCAGCAGTCTTTCGTTGAATTTTAGAGGGATATGCGGTGGAGGGCCTCCG
AGGCAGCGTTTCGCCGCATACCACATTTCGGAGGGCCGAAATCCATCCAAAACTATCAAG
TGGGACTAACACATGAACATACGTGTGTTGAGATTCTGAGATGCCCAAGAGCCAGCTCCC
GCGCGTGACCCACTTCACCGGCGACCGCTGCCACTTAGGAAGGTTCTTGACTGAAAAAGG
GAAAACTCCCACGATGGGTTCACCCGAGGAAATCTTGCGAGATCATGAGCTCAACCATTG
CTTTCCATGTTCCTATGAACTAACCAAACAATCAAGTGAAAATCCCATTGGCCACCGGTA
GTTTAAATAATTTCAGAAGCGTAGACCATGCTTCGGATGGCCAAAATCCACCTAAAACTT
GCAAGTGGGCCTAATATGTGTGTAAAAGTGTGCTGGGATGGTGAGGGGGCCAAGAGCTAG
CTAGCGTGGCGGCATGCTGTCGTGGGAGTAAGAAATCTCTGCACAGTGTGTTTTAGGG
```

FIGURE 1

```
CAACACTTGGCAAATGTGTGATCTTCGGAACATCCCAAGCTTGGGACCGTCAAGTTGCTT
TTGTGCGCAAAGTAAACGCAAAAAACATGCGCCACTCCTTTACCATATGCCGGACAAAAA
AAACTTGGCAAATGGTTATTTCCTTGGTGATCGGTGTTCTGCGCCGTATGCCGATGGTCG
ACATAGGCTTTGCCGTGTTCTGCGTTGCCTTTGTCGTGGCTTTTTCCCACATGGCAAATC
CATAATTTCCAGTAGTGACTCAATAATATTTGAAGGCAAGAACACCAGGGAGCCGAATTG
AATTTCCGGCATATCCGCTACTATAGATTGAAAATAAGGAGGCGGATCATCTCCTTGGTG
CAACCCCTTTTTTGTCTAAAAATAATTTTCTTTTTGAATATTTTACATTTCTTCATACTA
TAATTTTGGATACATAAAATATTAACTTTATATATGAAAATATAATTCCAATACTTTTGC
ACTCATCAAATAATTAATTTTGGATATATAACTAGTTGAGTTGTTTATGCAAAATTCCTA
TTAAATTATTTTCGGTACCAAACAATGTAAAATTAGTAAGGTCATAACTAGTTGTGCAAC
GTATACTGAAAAAATTAATTTTGGAATTTCGCAAAAAAAAAATGGATACATGGAACGCT
CAGGCGATGTCTGTGGCCATGAAACCGCGCTTGTCCTGTGCATAATTCTAGGGTGTGGGT
GCTTCTATAAATGGATAATGAGCATGCATCAGAACGCTCCAGCGATGTTTGTGGCCATGA
GACAGAGCTTGTCCGTGCATGCCTACGCGGCTCTCCCTCGCCGTGGCCCAAGCTCTGTTC
CCTTCCGACAGACCCGGCCGGTACAAGCGCCTGCGACATGGCCGAAGCGCCGCCCATCCG
CGCATAAATACCCGCACACCATCTATCACCGATTCACAACCAACAGCAGCAGCACACATA
TACACACAAGAACCATCCAACAAATCCAGAATGGCTTCCTCATCAAGCAGGATGCTGGCG
GCGGCGGCGCTGGCGGCGCTGTTCGTGGGCGCGATGTGCGAGGCCCCGTGACGTTCACG
GTAGAGAAGGGCTCCGACGAGAAGAACCTGGCGCTGTCGATCAAGTACAACAAGGAGGGC
GACTCCATGGCGGAGGTGGAGCTCAAGGAGCACGGCTCCAACGAGTGGCTGGCCCTGAAG
AAGAACGGCGACGGCGTGTGGGAGATCAAGAGCGACAAGCCGCTCAAGGGGCCATTCAAC
TTCCGCTTCGTGTCCGAGAAGGGGATGAGGAACGTGTTCGACGACGTGGTTCCGGCGGAG
TTCAAGGTCGGCACCACCTACAAGCCCGAGGAGTAGATCCGCCATCGGTCGTCATCGGAA
GTTTTCGATTTTCCTCATATCATGAATAATTTGTCGAGGTTTTTGTCAGTGAGGTGGTGA
TTGGGAGAAGCACAACTATGGATGTGCTTCCTAGTATCTCCCATGCACCCATTACCATGA
CCAATATTTTTTTATATGAATCGGNTTANGTAANTTAATTTAAAAGNCCCTTAAAAG
```

FIGURE 1 (cont.)

A
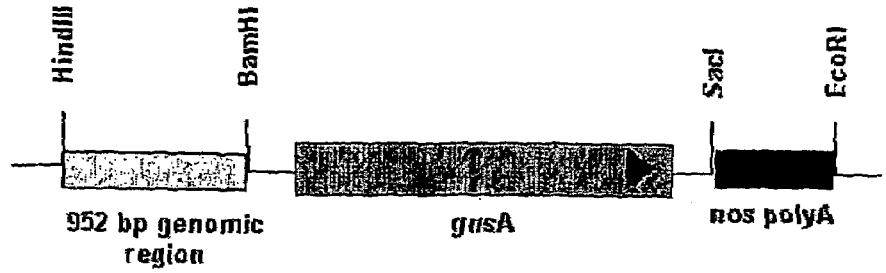
B
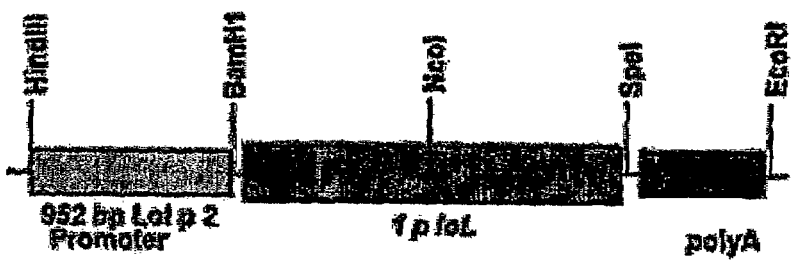
C
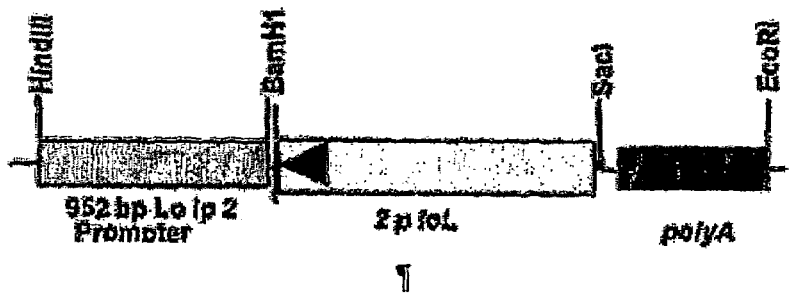
FIGURE 3

A
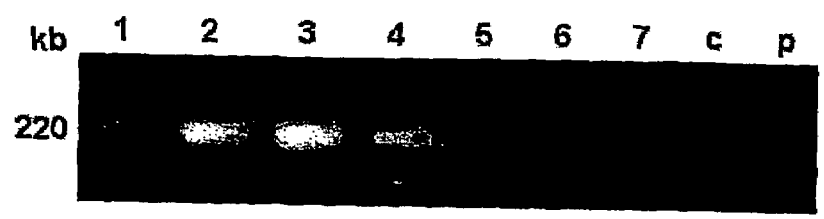
B
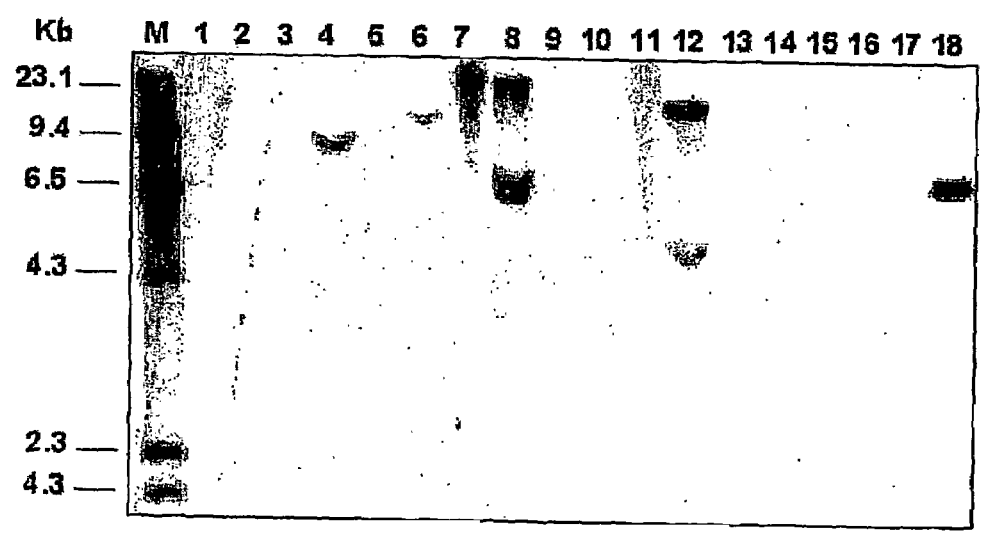
FIGURE 6

RYEGRASS POLLEN-SPECIFIC PROMOTERS AND EXPRESSION CONSTRUCTS

The present invention relates generally to an isolated nucleic acid molecule capable of modifying tissue-specific expression, preferably of a second nucleic acid molecule operably linked thereto. More particularly, the present invention is directed to an isolated nucleic acid molecule, capable of modifying pollen-specific expression, preferably of an operably linked second nucleic acid molecule. The present invention further contemplates constructs including the molecule and methods of using the molecule, including for example, the modification of gene expression in pollen, such as via down- or up-regulation, and the introduction into pollen of desired phenotypes.

Forage grasses are the backbone of sustainable agriculture and contribute extensively to the world economy. Two related genera, *Festuca* (fescues) and *Lolium* (ryegrasses) are of significant value in temperate grasslands. These genera contain well-adapted, very productive grasses widely distributed in temperate and cool climates in North and South America, Europe, Asia, Australia and New Zealand, where they are used for agricultural and recreational purposes (Jauhar 1993). The commercially most important ryegrasses in cool temperate climates throughout the world are Italian or annual ryegrasses. In New Zealand and Australia, perennial ryegrass is grown on more than 10 million ha providing high quality forage to support over 60 million sheep and cattle (Siegel et al. 1985). However, ryegrasses and other forage species are also responsible for a major portion of grass pollen allergies worldwide. Pollen allergy, in particular grass pollen allergy, is a major environmental disease that afflicts about 20% of the population in cool temperate climates.

Accordingly, there is a need for a means for the generation of useful agronomic plants having modified pollen-specific gene expression, for example plants that are inter alia male sterile and/or that produce low allergenic pollen.

In one aspect, the present invention provides an isolated nucleic acid molecule including a sequence of nucleotides selected from the group consisting of (a) a nucleotide sequence set forth in SEQ ID NO:2 or 3; (b) a sequence which hybridises to SEQ ID NO:2 or 3 under moderately stringent or high stringency conditions; (c) a complement of (a) or (b); and (d) a fragment or variant of (a), (b) or (c);

wherein said molecule is capable of modifying pollen-specific expression, preferably of an operably-linked second nucleic acid molecule.

The nucleic acid molecule may be obtained from ryegrass (*Lolium*) or fescue (*Festuca*) species. These species may be of any suitable type, including Italian or annual ryegrass, perennial ryegrass, hybrid ryegrass, tall fescue, meadow fescue and red fescue. Preferably the species is a ryegrass, more preferably perennial ryegrass (*L. perenne*). The nucleic acid molecule may also be a synthethic molecule.

A pollen-specific promoter has been isolated from *Lolium perenne*, which promoter shows useful properties for targeted pollen-specific expression. Such promoters are particularly useful in the production of low pollen allergen transgenic plants, for transgene containment and/or for the down-regulation of the expression of genes that are involved in pollen development to produce, for example, male sterile or infertile plants.

The modification of pollen-specific gene expression has many uses in plant breeding and development. For example, while the potential of biotechnology in the development of improved plant cultivars is now well recognised, the possibility for transgene escape to wild and non-transformed species raises commercial and ecological concerns. Accordingly, one possible use is in the development of mechanisms whereby transgenic plants are caused to be male infertile, thereby reducing the potential for cross-pollination with other, non-transgenic plants. The regulation of male fertility in plants also has other applications; for example, in the maintenance of uniformity and hybrid vigour of F1 hybrid plants by ensuring that self-pollination is minimised during seed production.

In other instances, it may be desirable to modify pollen-specific gene expression in order to reverse sterility.

In still other cases, it may be desirable to generate hybrids, for example by crossing a plant, which has been caused to be male infertile, with another fertile plant, upon which has been conferred pollen-specific expression of a desired trait.

Another possible use relates to the high pollen allergen production of certain plant species. The ability to modify pollen gene expression would permit manipulation of the production of pollen allergens by plants, thereby facilitating the development of plants causing reduced pollen allergenicity.

As used herein, the term "isolated" means that the material is removed from its original environment (eg. the natural environment if it is naturally occurring). For example, a naturally occurring nucleic acid fragment present in a living plant is not isolated, but the same nucleic acid fragment separated from some or all of the coexisting materials in the natural system, is isolated. Such an isolated nucleic acid fragment could be part of a vector and/or such nucleic acid fragments could be part of a composition, and still be isolated in that such a vector or composition is not part of its natural environment.

The term "isolated" also encompasses synthetic molecules, for example of a hybrid or modular promoter.

By "variant" in respect of a nucleotide sequence is meant, for example, an analogue, derivative or mutant, which remains capable of modifying pollen-specific expression, preferably of an operably-linked second nucleic acid molecule.

Such variants include naturally occurring allelic variants and non-naturally occurring variants. Additions, deletions, substitutions and derivatizations of one or more of the nucleotides are contemplated so long as the modifications do not result in loss of functional activity of the variant. Preferably the variant has at least approximately 80% identity, such as for example 81%, 82%, 83%, 84%, 85%, 86%, 87%, 88% or 89% identity to the relevant part of the above mentioned sequence, more preferably at least approximately 90%, such as for example 91%, 92%, 93% or 94%, identity, most preferably at least approximately 95% identity, such as for example 96%, 97%, 98%, 99% and 100% identity.

The present invention also extends to variants of the nucleic acid molecule of the present invention, which variants are from a ryegrass (*Lolium*) or fescue (*Festuca*) species, and which variants have a corresponding coding region with at least approximately 80% identity, such as for example 81%, 82%, 83%, 84%, 85%, 86%, 87%, 88% or 89% identity, more preferably at least approximately 90% identity, such as for example 91%, 92%, 93% or 94%, identity, most preferably at least approximately 95% identity, such as for example 96%, 97%, 98%, 99% and 100% identity to the coding sequence shown in FIG. 1 hereto.

By "fragment" in respect of a nucleotide sequence is meant a part of the nucleic acid molecule, which remains capable of modifying pollen-specific expression, preferably of an operably-linked second nucleic acid molecule. Such fragments may have a size of, for example, at least approximately 15 nucleotides, at least approximately 30 nucleotides, at least approximately 45 nucleotides, at least approximately 100 nucleotides, or at least approximately 200 nucleotides.

In a particularly preferred embodiment the fragment may include one or more sequences selected from the groups consisting of:

```
AGGTCA        (Zm13 Q element;;       SEQ ID NO: 4)
TGTGGTTATATA  (LAT52 element;;        SEQ ID NO: 5)
and GTGA          (GTGANTGIO element;.    SEQ ID NO: 6)
```

By "operably-linked" is meant that the nucleic acid molecule of the present invention is capable of causing expression of a second or further nucleic acid molecule in a plant cell. Usually, the nucleic acid molecule is upstream of the second or further nucleic acid molecule. Where a terminator is operably-linked, the terminator is capable of terminating the expressed transcript of the second or further nucleic acid molecule. Usually, the terminator is downstream of the second or further nucleic acid molecule.

By "expression" is meant that a relevant nucleic acid molecule is transcribed and optionally translated. Thus, the term "expression" can relate both to the transcription of ribonucleic acid (RNA) from the DNA, as well as the transcription of RNA followed by the translation of that RNA into an amino acid sequence. Modifying expression includes, for example the situation where the nucleic acid molecule of the present invention is used to down-regulate expression of an endogenous gene, for example using antisense or sense suppression technology, or interfering RNA (RNAi) or hairpin approaches. Modifying expression also includes use of the nucleic acid molecule of the present invention to express a protein encoded by an existing endogenous gene or to introgress an exogenously-derived sequence and optionally express protein therefrom.

By "pollen-specific" is meant that the expression is substantially confined to the pollen.

"Moderately stringent conditions" or "high stringency conditions" for hybridization may be identified as described by Sambrook et al, 1989, the relevant disclosure of which is incorporated herein by reference.

Such conditions are readily determinable by a person skilled in the art, and are generally an empirical calculation based on probe length, salt concentration and washing temperature. For example, the use of a washing solution including approximately 0.7 to approximately 0.2×SSC (standard sodium citrate), at approximately 50° C. to approximately 60° C., would generally be considered moderately stringent conditions. For example, the use of a washing solution including approximately 0.2 to approximately 0.1×SSC at approximately 60° C. to approximately 70° C. would generally be considered high stringency conditions.

Reference herein to a "gene", "second nucleic acid molecule" or "further nucleic acid molecule" is to be taken in its broadest context and includes a deoxyribonucleic acid (DNA) sequence which is capable of having its expression modified by the nucleic acid molecule of the present invention. As referred to above, the term "expression" can relate both to the transcription of ribonucleic acid (RNA) from the DNA, as well as the transcription of RNA followed by the translation of that RNA into an amino acid sequence.

Accordingly, a gene, second or further nucleic acid molecule includes within its scope both a DNA coding for an aminoacid encoding RNA (i.e. mRNA) as well as a DNA encoding a RNA that does not code for an amino acid sequence. Such an RNA that does not code for an amino acid sequence may include an antisense RNA. A gene, second or further nucleic acid molecule may be of a wild-type or altered form. In the case of an altered form, the sequence may be modified by alterations to the nucleotide sequence.

In a preferred embodiment of this aspect of the invention, the further nucleic acid molecule is a sequence, for example a gene or fragment thereof, capable of modifying expression of a pollen allergen, preferably capable of causing downregulation of expression of a pollen allergen. Preferably the pollen allergen is Lol p 1 and/or Lol p 2.

In a preferred embodiment of this aspect of the invention, the isolated nucleic acid molecule includes the nucleotide sequence shown in SEQ ID NO:2 or 3 or a fragment or variant thereof. In a particularly preferred embodiment, the fragment or variant may include the nucleotide sequence shown in SEQ ID NO:2 or 3, modified so that the final nucleotide in the terminal 3' nucleotide sequence CCAGA is deleted and the penultimate nucleotide in that sequence is modified such that the sequence is CCAC.

In a particularly preferred embodiment the fragment may include one or more sequences selected from the groups consisting of:

```
AGGTCA        (Zm13 Q element;;       SEQ ID NO: 4)
TGTGGTTATATA  (LAT52 element;;        SEQ ID NO: 5)
and GTGA          (GTGANTGIO element;.    SEQ ID NO: 6)
```

In a further aspect of the present invention there is provided a construct including a nucleic acid molecule according to the present invention.

The term "construct" as used herein refers to an artificially assembled or isolated nucleic acid molecule, which includes the nucleic acid molecule of the present invention. In general a construct may also include further nucleic acid molecule(s) of interest, a marker gene which in some cases may also be the further nucleic acid molecule of interest and other appropriate regulatory sequences. It should be appreciated that the inclusion of these other regulatory sequences in the construct is optional, for example, such sequences may not be required in situations where the regulatory sequences of a host cell are to be used. The term construct includes vectors but should not be seen as being limited thereto. The term construct also includes chimeric genes.

The term "vector" as used herein encompasses both cloning and expression vectors. Vectors are often recombinant molecules containing nucleic acid molecules from several sources.

Accordingly, the construct may be a vector. In a preferred embodiment of this aspect of the invention, the vector may include a further nucleic acid molecule, for example a gene or fragment thereof, a nucleic acid molecule according to the present invention and a terminator; said nucleic acid molecule, further nucleic acid molecule and terminator being operably-linked.

In a preferred embodiment of this aspect of the invention, the further nucleic acid molecule is a sequence, for example a gene or fragment thereof, capable of modifying expression of a pollen allergen, preferably capable of causing downregulation of expression of a pollen allergen. Preferably the pollen allergen is Lol p 1 and/or Lol p 2.

In another embodiment, the vector may include more than one further nucleic acid molecule. The further nucleic acid molecules within the same vector may have identical or differing sequences. In a particularly preferred embodiment, each further nucleic acid molecule has one or more upstream nucleic acid molecules according to the present invention and one or more downstream terminators, although expression of more than one further nucleic acid molecule from an upstream nucleic acid molecule or termination of more than one further nucleic acid molecule from a downstream terminator(s) is not precluded.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, or integrative or viable in the plant cell.

The terminator may be of any suitable type and may be endogenous to the target plant cell or may be exogenous, provided that it is functional in the target plant cell. A variety of terminators which may be employed in the vectors of the present invention are well known to those skilled in the art. The terminator may be from the original genomic sequence from which the promoter sequence was isolated or a different genomic sequence. Particularly suitable terminators are polyadenylation signals, such as the CaMV 35S polyA and other terminators from the nopaline synthase (nos) and the octopine synthase (ocs) genes.

The vector may include further elements necessary for expression of the further nucleic acid molecule, in different combinations, for example vector backbone, origin of replication (ori), multiple cloning sites, spacer sequences, enhancers, introns [such as the maize Ubiquitin Ubi intron], antibiotic resistance genes and other selectable marker genes (such as the neomycin phosphotransferase (npt2) gene, the hygromycin phosphotransferase (hph) gene, the phosphinothricin acetyltransferase (bar or pat) gene], and reporter genes [such as beta-glucuronidase (GUS) gene (gusA)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical GUS assays, northern and western blot hybridisation analyses.

Those skilled in the art will appreciate that the various components of the vector are operably-linked, so as to result in expression of said further nucleic acid molecule(s) gene or genes. Techniques for operably linking the components of the vector of the present invention are well known to those skilled in the art. Such techniques include the use of linkers, such as synthetic linkers, for example including one or more restriction enzyme sites.

The construct may be a chimeric gene. Accordingly, in a further aspect of the present invention there is provided a chimeric gene including a nucleic acid molecule of the present invention operably linked to further nucleic acid molecule(s) capable of causing down-regulation of expression of a pollen allergen, for example a gene or genes encoding one or more pollen allergens or a fragment thereof. Preferably, the pollen allergens are the major pollen allergens Lol p 1 and/or Lol p 2. The sequence of the further nucleic acid molecule may be in either a sense or antisense orientation when operably linked with the nucleic acid molecule of the present invention. In a preferred embodiment, the chimeric gene is included in a vector which may be used to transform a plant cell.

The constructs, vectors and chimeric genes of the present invention may be incorporated into a variety of plants, including: monocotyledons, such as grasses from the genera *Lolium, Festuca, Paspalum, Pennisetum, Panicum* and other forage and turfgrasses, corn, rice, sugarcane, oat, wheat and barley; dicotyledons, such as arabidopsis, tobacco, soybean, canola, cotton, potato, chickpea, medics, white clover, red clover, subterranean clover, alfalfa, eucalyptus, poplar, and hybrid aspen; and gymnosperms, such as pine tree. In a preferred embodiment, the vectors may be used to transform monocotyledons, preferably grass species such as ryegrasses (*Lolium* species) and fescues (*Festuca* species), even more preferably perennial ryegrass (*Lolium perenne*), Italian ryegrass (*Lolium multiflorum*) and hybrid ryegrass (*Lolium× boucheanum*), including forage- and turf-type cultivars.

Techniques for incorporating the constructs, vectors and chimeric genes of the present invention into plant cells (for example by transduction, transfection or transformation) are known to those skilled in the art. Such techniques include *Agrobacterium*-mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed. Other considerations include the ease of transformation, type of tissue and number of gene inserts required.

Cells incorporating the constructs, vectors and chimeric genes of the present invention may be selected, as described above, and then cultured in an appropriate medium to regenerate transformed plants, using techniques well known in the art. The culture conditions, such as temperature, pH and the like, will be able to be determined without undue experimentation by the person skilled in the art. The resulting plants may be reproduced, either sexually or asexually, using methods known in the art, to produce successive generations of transformed plants.

In a further aspect of the present invention there is provided a plant cell, plant, plant seed or other plant part, including, e.g. transformed with, a nucleic acid molecule, construct, vector or chimeric gene of the present invention.

The plant cell, plant, plant seed or other plant part may be from any suitable species, including monocotyledons, dicotyledons and gymnosperms. In a preferred embodiment the plant cell, plant, plant seed or other plant part is from a monocotyledon, preferably a grass species, more preferably a ryegrass (*Lolium* species) or fescue (*Festuca* species), even more preferably perennial ryegrass (*Lolium perenne*), Italian ryegrass (*Lolium multiflorum*) and hybrid ryegrass (*Lolium× boucheanum*), including both forage- and turf-type cultivars.

The present invention also provides a plant, plant seed or other plant part derived from a plant cell of the present invention. The present invention also provides a plant, plant seed or other plant part derived from a plant of the present invention.

In a further aspect of the present invention there is provided a low allergy plant including a nucleic acid molecule, construct, vector or chimeric gene of the present invention. In a preferred embodiment, the low allergy plant is a ryegrass or fescue.

In a further aspect of the present invention there is provided a method of modifying gene expression in pollen, said method including introducing into a plant cell an effective amount of a nucleic acid molecule, construct, vector or chimeric gene according to the present invention.

By "an effective amount" is meant an amount sufficient to result in an identifiable phenotypic trait in the plant cell, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Sambrook et al, 1989, the relevant disclosure of which is incorporated herein by reference.

In a preferred embodiment of this aspect of the present invention, the nucleic acid molecule according to the present invention is used to direct the pollen-specific expression of a further nucleic acid molecule to down-regulate the expression of pollen allergens in the plant. Down-regulation may be achieved via any one of a range of known techniques, readily available to a person skilled in the art, including for example antisense and sense suppression technology, and other gene silencing technologies such as via the use of interfering RNA. Preferably, the allergen is selected from the major pollen allergens Lol p 1 and Lol p 2. The sequence of the further nucleic acid molecule may be in either a sense or antisense orientation when operably linked with the nucleic acid molecule of the present invention. Alternatively, the further nucleic acid molecule may be incorporated as multiple copies, in either orientation, in a range of possible RNAi-generating constructs. RNAi technology has been described in a wide range of publications including, for example, Fire, A. et al (1998); Caplan, N. et al (2000); U.S. Pat. No. 6,506,559; International patent applications WO 99/53050 and WO 99/49029; and U.S. Pat. No. 6,573,099.

Using the methods and materials of the present invention, genes may be targeted for expression in pollen, or the expression of pollen-specific genes may be modified. For example, gene expression may be facilitated in pollen by placing a copy or copies of a further nucleic acid molecule, for example the gene to be expressed or a fragment thereof, operably under the control of the nucleic acid molecule according to the present invention. Furthermore, a nucleic acid molecule of the present invention may be used to introduce a further nucleic acid molecule, for example a gene or fragment thereof, into a plant for specific purposes such as introducing male sterility. Alternatively, decreased expression of an endogenous pollen-specific gene may be achieved by placing a sense or antisense nucleic acid molecule or dsRNA or small interfering RNA (siRNA) derived from the gene operably under the control of the nucleic acid molecule according to the present invention.

In a further aspect of the present invention there is provided a method of producing a plant with reduced male fertility compared with a wild type plant, said method including introducing into the plant a nucleic acid molecule of the present invention in combination with a further nucleic acid molecule capable of modulating male fertility. Preferably the plant is a male sterile plant. In a preferred embodiment, the further nucleic acid molecule may be capable of modifying pollen development, even more preferably the further nucleic acid molecule may be involved in and is preferably a gene or a fragment thereof critical to pollen development. In a further preferred embodiment, the expression of the further nucleic acid molecule may result in cell death at the site of expression. In a further preferred embodiment the further nucleic acid molecule may encode the bacterial ribonuclease barnase or a fragment thereof. The use of the nucleic acid molecule according to the present invention may enable the specific expression of the relevant gene in pollen, reducing any unwanted side-effects of expression in other plant tissues.

In a further aspect of the present invention there is provided a plant with reduced male fertility compared with a wild type plant, preferably a male sterile plant, produced according to the methods according to the present invention. Such plants may be used to develop a transgene containment system by reducing pollen fertility. Furthermore, such plants may be used in hybrid seed production.

In a further aspect of the present invention there is provided a preparation for transforming a plant including a nucleic acid molecule according to the present invention. The preparation may contain vectors or other constructs to facilitate administration to and/or transformation of the plant with the nucleic acid molecule.

The present invention will now be more fully described with reference to the accompanying Examples and drawings. It should be understood, however, that the description following is illustrative only and should not be taken in any way as a restriction on the generality of the invention described above.

In the Figures:

FIG. 1 shows sequence of genomic clone (SEQ ID NO:1) showing putative promoter (SEQ ID NO:2) and coding regions. Italics (and partially bold): 952 bp of genomic sequence (SEQ ID NO:3); doubly underlined: coding sequence; bold italics, dashed underlined: primer D21pr1L; bold italics: primer D21pr1R (partially doubly underlined). Also shown is the SacI restriction site (bold) and several stop codons in the coding region of the gene (bold underlined).

FIG. 2 shows the analysis of promoter elements of the 952 bp genomic region of the pollen-specific promoter from perennial ryegrass; Zm13 Q element (solid arrowheads), LAT52 element (outlined arrowheads) and GTGANTG10 element (hatched arrowhead).

FIG. 3 shows chimeric vectors containing the 952 bp genomic region. A pLp952:GUS fusion vector driven by the 952 bp genomic region pBS-260gn (Hamilton et al. 1992) was used as the basis for the construction of the promoter-reporter cassette for plant cell transformation using PEG-mediated transformation techniques. PBS-260gn contains the GUS reporter gene (Jefferson et al. 1987) and the nopaline synthase (nos) terminator sequence. B Vector containing Lol p 1 in an antisense orientation driven by the 952 bp genomic region (pLP2-asLolp1). C Vector containing Lol p 2 in an antisense orientation driven by the 952 bp genomic region (pLP2-asLolp2).

FIG. 4 shows chimeric vectors for gene silencing based on the formation of double-stranded RNA using the 952 bp genomic region of the pollen-specific promoter from perennial ryegrass from the present invention. A Vector containing inverted repeats of ca. 200 bp fragment of Lol p 1 with LpCCR1 intron. B Vector containing inverted repeats of ca. 200 bp fragment of Lol p 2 with LpCCR1 intron. C Vector containing inverted repeats of combined ca. 200 bp fragments of Lol p 1 and Lol p 2 with LpCCR1 intron.

FIG. 5 shows steps involved in the generation of transgenic tobacco using direct PEG-mediated gene transfer. A tobacco protoplasts. B Callus regenerated from tobacco protoplasts. C Putative transgenic tobacco plantlets on selective medium. D Putative transgenic tobacco on root-inducing medium.

FIG. 6A shows PCR analysis of transgenic tobacco plants containing the Lp952GUS construct using GUS specific (gusA) primers B. Southern hybridisation of the PCR positive plants showing the stable integration of gusA (Probe: gusA).

Figure 8:

FIG. 8 shows steps involved in the generation of transgenic ryegrass to down-regulate the expression of pollen allergens using used to direct the pollen-specific expression of a gene to down-regulate the expression of pollen allergens. A Immature perennial ryegrass inflorescence. B-F Development of callus from immature perennial ryegrass inflorescence. G Immature inflorescence-derived callus spread on filter disc ready for particle bombardment. H particle delivery system. I, J Regenerating perennial ryegrass plantlets on selective medium. K Putative transgenic perennial ryegrass plantlets on root-inducing medium. L Putative transgenic perennial ryegrass plants under containment glasshouse conditions.

EXAMPLE 1

Cloning of a Novel Promoter

Figure 2:
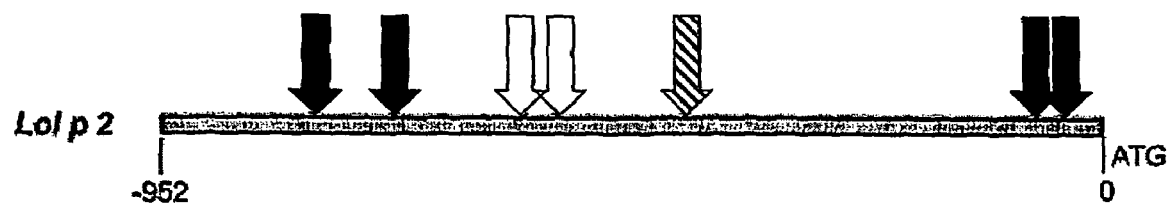

In one embodiment of the present invention, a promoter sequence was isolated from a ryegrass gene. A 3.9 kb fragment of genomic sequence was isolated from a Lambda-DASH II (Stratagene) genomic library constructed from four-week-old perennial ryegrass (*Lolium perenne* L.) cv. Barlano after hybridisation screening of the genomic library with a Lol p 2 cDNA sequence. Positive plaques from the tertiary screen were amplified and purified phage DNA was isolated. The genomic region was fully sequenced (FIG. 1) and found to contain 3.3 kb including approximately 2.7 kb 5' promoter region and 567 bp of gene sequence which, has an ORF of 366 bp and encodes a small protein of 122 amino acids. Promoter elements of the 952 bp genomic region of the pollen-specific promoter from perennial ryegrass are shown (FIG. 2).

EXAMPLE 2

Construction of Chimeric Gene Vectors

A PCR product containing 952 bp of promoter region (SEQ ID NO:3) was produced using standard PCR conditions. The sequences of the primers follow.

```
D21pri1L:
5'-AAAAGTGTGCTGGGATGGTG-3'         (SEQ ID NO: 7)

D21pri1R:
5'-CCATCCAACAAATCCAGAATGGCTTCC-3'  (SEQ ID NO: 8)
```

The 952 bp PCR product was purified, subcloned into pGEMTeasy (Promega), and sequenced to check for PCR amplification errors. A construct was made using the above PCR product as a promoter in fusion with the reporter gene β-glucuronidase (GUS) coding sequence (gusA) depicted in FIG. 3A.

The 952 bp PCR product was also used to construct vectors containing the pollen allergen encoding sequences Lol p 1 (FIG. 3B) and Lol p 2 (FIG. 3C) in antisense orientation. These vectors were designed to be capable of silencing the corresponding endogenous genes.

Figure 4:
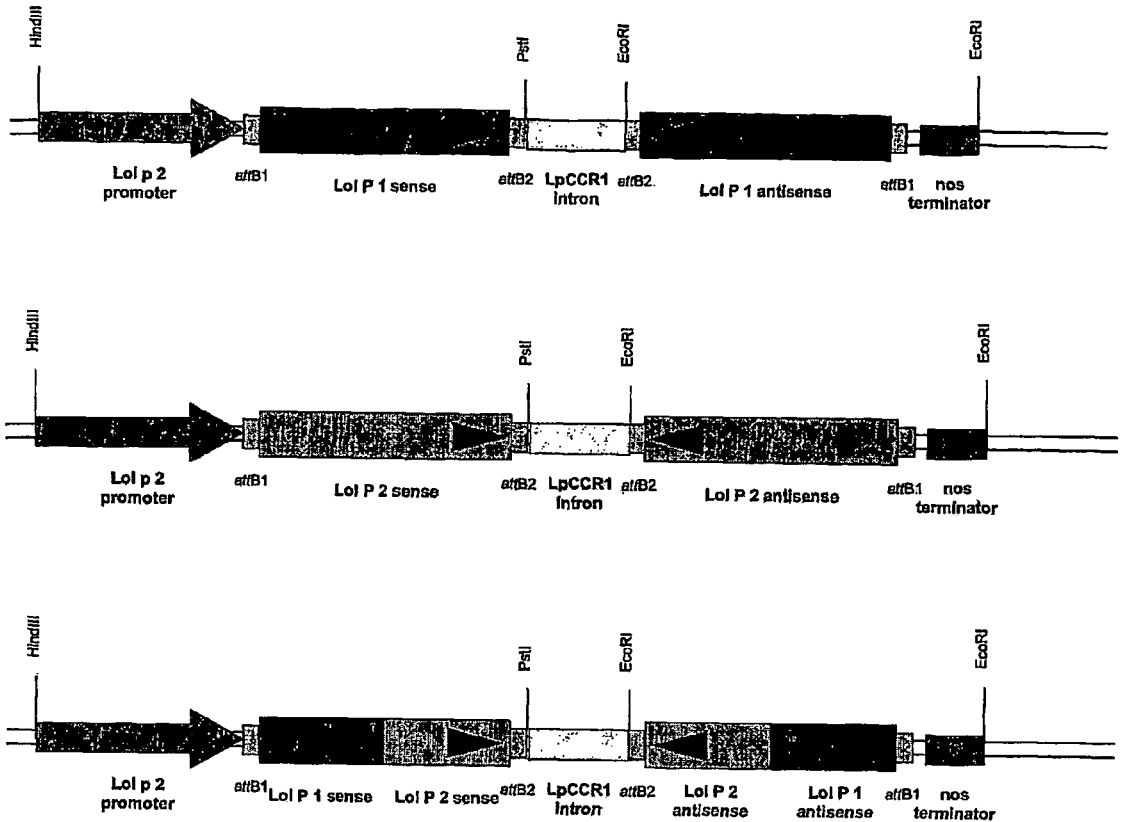

Additionally, gene silencing vectors based on the formation of double-stranded RNA are designed and constructed using the 952 bp PCR product as the regulatory element and short inverted repeats of Lol p 1, Lol p 2 and Lol p 1+Lol p 2 separated by a perennial ryegrass intron (FIG. 4).

EXAMPLE 3

The Generation of Transgenic Tobacco Plants for Analysis of Expression Patterns Directed by Novel Promoter The chimeric GUS fusion vector of Example 1 was transgenically expressed in the heterologous system, tobacco, in order to assess the expression pattern directed by the 952 bp genomic region. Transgenic tobacco plants were generated by PEG mediated direct gene transfer (DGT) of tobacco protoplasts as described in detail below.

A. Isolation of Mesophyll Protoplasts from Tobacco Shoot Cultures

Fully expanded leaves (2-4) of a 6 week-old shoot culture were placed under sterile conditions in a 9 cm plastic culture dish containing 12 ml enzyme solution [1.0% (w/v) cellulase "Onozuka" R10 and 1.0% (w/v) Macerozyme® R10]. The leaves were wetted thoroughly with enzyme solution and the mid-ribs removed. The leaf halves were cut into small pieces and incubated overnight (14-18 h) at 25° C. in the dark without shaking.

The protoplasts were released by gently pipetting up and down, and the suspension poured through a 100 μm stainless steel mesh sieve on a 100 ml glass beaker. The protoplast suspension was mixed gently, distributed into two 14 ml sterile plastic centrifuge tubes and carefully overlayed with 1 ml W5 solution (Spangenberg et al 1988). After centrifugation for 5 min. at 70 g (Clements Orbital 500 bench centrifuge, swing-out rotor, 400 rpm), the protoplasts were collected from the interphase and transferred to one new 14 ml centrifuge tube. 10 ml W5 solution were added, the protoplasts resuspended by gentle tilting the capped tube and pelleting, as before. The protoplasts were resuspended in 5-10 ml W5 solution and the yield determined by counting a 1:10 dilution in a haemocytometer.

B. Direct Gene Transfer to Protoplasts Using Polyethylene Glycol

The protoplasts were pelleted [70 g at 400 rpm for 5 min.] and resuspended in transformation buffer to a density of $1.6 \times 10^6$ protoplasts/ml. Care was taken to carry over as little as possible W5 solution into the transformation mix. Samples (300 μl) of the protoplast suspension (ca. $5 \times 10^5$ protoplasts) were aliquoted in 14 ml sterile plastic centrifuge tubes, and 30 μl of transforming DNA were added. After carefully mixing, 300 μl of PEG solution (Spangenberg et al 1988) were added and mixed again by careful shaking. The transformation mix was incubated for 15 min. at room temperature with occasional shaking. 10 ml W5 solution were gradually added, the protoplasts pelleted [70 g at 400 rpm for 5 min.] and the supernatant removed. The protoplasts were resuspended in 0.5 ml K3 medium (Spangenberg et al 1988), ready for cultivation.

C. Culture of Protoplasts, Selection of Transformed Lines and Regeneration of Transgenic Tobacco Plants Approximately $5 \times 10^5$ protoplasts were placed in a 6 cm petri dish. Pre-warmed (melted and kept in a water bath at 40-45° C.) 1:1 mix of K3:H medium (4.5 ml) (Spangenberg et al 1988) containing 0.6% SeaPlaque™ agarose were added and, after gentle mixing, allowed to set.

After 20-30 min the dishes were sealed with Parafilm® and the protoplasts were cultured for 24 h in darkness at 24° C., followed by 6-8 days in continuous dim light (5 µmol $m^{-2}$ $s^{-1}$, Osram L36 W/21 Lumilux white tubes), during which time first and multiple cell divisions occurred. The agarose containing the dividing protoplasts was cut into quadrants and placed in 20 ml of A medium (Spangenberg et al 1988) in a 250 ml plastic culture vessel. The corresponding selection agent was added to a final concentration of 50 mg/l kanamycin sulphate (for npt2 expression) or 25 mg/l hygromycin B (for hph expression). Alternatively, selection may be carried out using 20 mg/l phosphinotricin (for bar expression). Samples were incubated on a rotary shaker with 80 rpm and 1.25 cm throw at 24° C. in continuous dim light.

Figure 5:
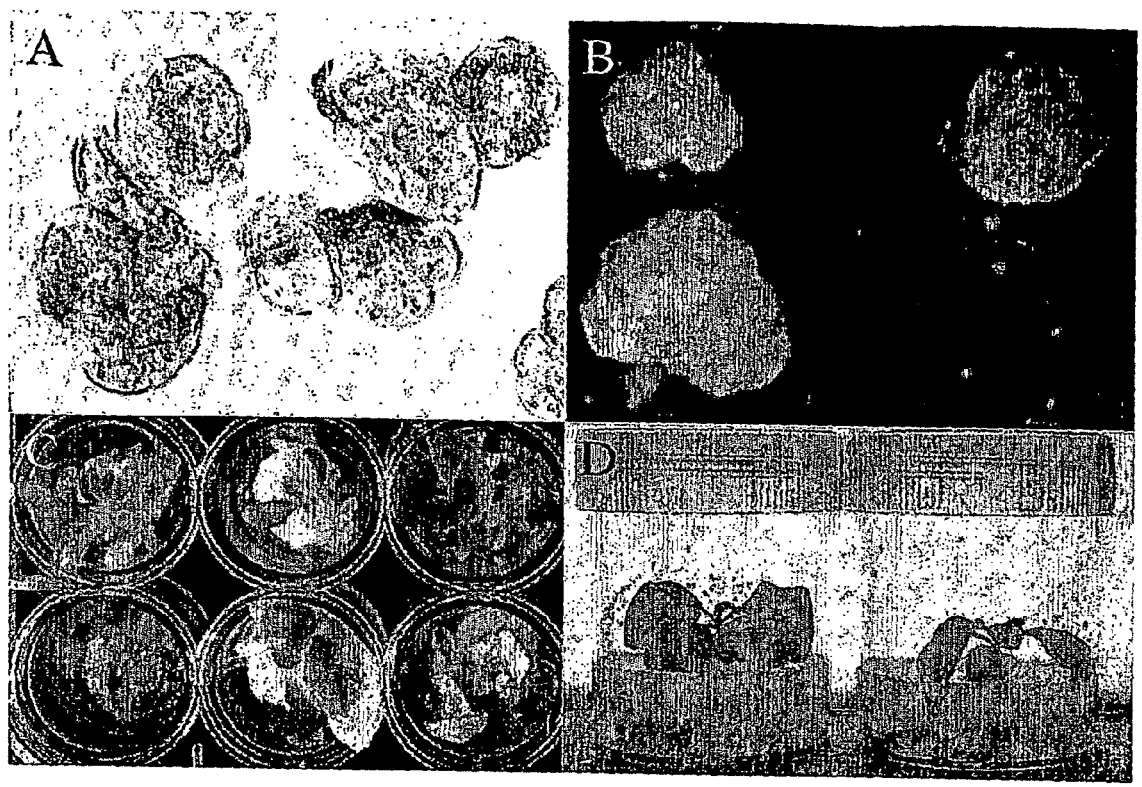

Resistant colonies were first seen 3-4 weeks after protoplast plating, and after a total time of 6-8 weeks protoplast-derived resistant colonies (when 2-3 mm in diameter) were transferred onto MS morpho medium (Spangenberg et al 1988) solidified with 0.6% (w/v) agarose in 12-well plates and kept for the following 1-2 weeks at 24° C. in continuous dim light (5 µmol $m^{-2}$ $s^{-1}$, Osram L36 W/21 Lumilux white tubes). During this time, calli proliferated and reached a size of 8-10 mm; shoots that were rooted on MS hormone free medium (Spangenberg et al 1988) differentiated and transgenic tobacco plants were recovered. (FIG. 5).

The putative transgenic tobacco plants were screened by PCR and Southern hybridisation analysis. The PCR screening was undertaken using gusA specific primers for the initial identification of transformed plants (FIG. 6A). The presence of the gusA gene was demonstrated by PCR-amplification of a 270 bp fragment using the forward primer:

```
5'-CTTTAACTATGCCGGGATCCATCG-3'    (SEQ ID NO: 9)
``` and the reverse primer:

```
5'-TAACCTTCACCCGGTTGCCAGAGG-3'.   (SEQ ID NO: 10)
```

The PCR positive transgenic plants were then analysed by Southern hybridisation to show stable integration of the transgene (FIG. 6B). For Southern hybridisation analysis, genomic DNA was extracted from lyophilised plant material using a CTAB-based protocol. DNA samples (10-15 µg) were digested with BamHI, HindIII, EcoRI, or XhoI restriction enzymes. The resulting DNA fragments were separated on a 1% agarose gel and transferred to Hybond N (Amersham Pharmacia Biotech) membranes. Hybridisation was performed according to the manufacturer's instructions and incorporation of DIG-dUTP into DNA probes and detection of bound probes was performed using the DIG Luminescent Detection Kit (Roche Diagnostics Cat. No 1363514) following the supplier's protocol. Hybridisation conditions were: 4×SSC, 50% (v/v) formamide, 0.1%. (w/v) N-lauroyl-sarcosine, 0.02% (w/v) SDS, and 2% (v/v) blocking solution at 42° C. Membranes were washed twice in 2×SSC/0.1% (w/v) SDS for five minutes at 25° C. then 0.2×SSC/0.1% (w/v) SDS followed by 0.1×SSC/0.1% (w/v) SDS, both for fifteen minutes at 68° C. Southern positive plants were transferred to soil and grown under glasshouse conditions until flowering.

EXAMPLE 4

Assay Promoter Activity in Plant Cells Under Stable Conditions

Figure 7:
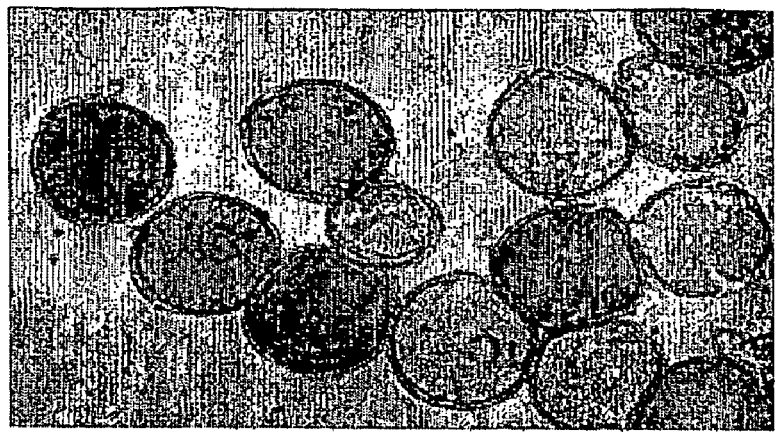
FIG. 7 shows GUS histochemical staining of pollen collected from transgenic tobacco plants containing the Lp952GUS construct.

Tissue samples were collected from the Southern positive plants and screened by histochemical GUS assays to assess the expression pattern of the 952 bp *Lolium perenne* promoter. Expression of the gusA reporter gene was observed exclusively in the pollen grains of the transgenic tobacco plants containing the 952 bpGUS fusion (FIG. 7).

These results indicate that the 952 bp region of *Lolium perenne* genomic sequence confers strong pollen-specific expression to the gusA gene coding sequence and is thus a pollen-specific promoter that represents an excellent candidate for applications requiring targeted gene expression to pollen cells such as, for example, transgene containment and/or the down-regulation of pollen allergen genes and/or induction of male sterility.

EXAMPLE 5

The Generation of Transgenic Perennial Ryegrass Plants for Down-Regulation of Pollen Allergens Using Chimeric Genes Under Control of the Novel Pollen-Specific Promoter The steps in the production of transgenic ryegrass plants for the down-regulation of main pollen allergens Lol p 1 and Lol p 2, using chimeric genes under control of pollen-specific promoter, are shown in FIG. 8.

A. Production of Target Material for Biolistic Transformation

Multi-tillered, well-established donor plants, generated from seedlings, are vernalised at less than 10° C. (minimum 4° C.) under an 8 hour day length for a period greater than 8 weeks. Flowering of plants is induced by growing at 24° C. under an increased day length of greater than 12 hours (optimum 16 hours).

Plants are monitored daily after the first 2-3 days of induction and floral tillers identified for harvest. Target immature inflorescences should be whitish in colour and no longer than 0.5 mm in length.

Selected floral tillers are harvested by cutting just below the base node and before the youngest leaves. The tillers are stripped of all leaf material and collected in one clean plastic vessel. For sterilisation, the collection vessel is filled with a sterilisation solution containing 5% available chlorine with 5 drops of Tween 20 for every 100 ml to ensure adequate sterilisation of plant material. Sterilisation of tillers is achieved by medium-to-high speed shaking for 20 minutes on a bench top platform shaker.

Subsequently, tillers are rinsed thoroughly with sterile distilled water and transferred in batches of 8-10 on to sterilized sheets of A5 paper.

Immature inflorescence are prepared, cut free from the base node and transferred to calli induction medium, LP5 [MS Macro, MS Micro, MS Vitamins (MS hormone free) with 5 mg/l 2,4-Dichlorophenoxyacetic acid and 30 g/l maltose]+250 mg/l cefotaxime. If the inflorescence in not intact (most likely in 2 pieces due to the cut), pieces may be plated individually.

All dishes are sealed with parafilm and incubated in the dark at 24° C. for up to 8 weeks to induce calli development.

B. Preparation of Embryogenic Calli for Microprojectile Bombardment

Embryogenic, friable, yellowish calli (1-2), derived from plated immature inflorescences, are transferred onto media-covered filter paper. Calli are squashed to yield an even, fine layer of cells across the disc surface and incubated for 4-6 hours at room temperature to prepare cells for bombardment.

C. Preparation of Particles for Microprojectile Bombardment

To a sterile 1.5 ml Eppendorf tube, 10 μl transforming DNA (1 μg/μl; gene of interest), 10 μl selectable marker (1 μg/μl), 100 μl gold particle solution (60 mg/ml), 100 μl 2.5 M $CaCl_2$ and 40 μl 100 mM spermidine are added, vortexed for 1 minute and allowed to sediment for 1 minute. The supernatant is removed, particles are resuspended in 900 μl 100% (w/v) filter-sterilized ethanol and mixed. The washed particles are sedimented and the washing step is repeated. The particles are then resuspended in 200 μl 100% (w/v) filter-sterilized ethanol.

D. Microprojectile Bombardment of Immature Inflorescence-Derived Calli Using a Biorad Particle Delivery System Microcarriers are soaked in 100% (w/v) isopropanol for 30 minutes, air-dried, embedded in autoclaved macrocarriers and transferred to a U.V.-sterilized tip box containing dehydrated silica gel. Prepared particles (20 μl) are then loaded to the centre of a microcarrier and air-dried. Particles prepared as detailed in Section C above, are then delivered to the target material, following the particle delivery systems manufacturers instructions.

Plates are subsequently sealed with parafilm and incubated in the dark at 50° C. overnight.

E. *Agrobacterium*-Mediated Transformation of Embryogenic Callus

The embryogenic material obtained as described above can alternatively be used for *Agrobacterium*-mediated transformation. Sample tissues are inoculated by vacuum infiltration with an *Agrobacterium* suspension ($O.D._{600}$ 0.3-1.0) in a modified liquid M medium (Spangenberg et al 1995) (AA major inorganic salts, AA amino acids and vitamins, 2% (w/v) sucrose, 3% (w/v) sorbitol, 0.2 mg/L kinetin, 0.1 mg/L gibberellic acid, 6.8 μM 2,4-D and 100 μM acetosyringone). Sample tissues are then transferred to sterile dry filter paper for 3 days in the dark at 21° C. Selection and regeneration are as described in Section F, below.

F. Selection of Transformed Calli and Regeneration of Transgenic Ryegrass Plants Filter paper discs containing bombarded calli are transferred to solidified proliferation media, LP3 [MS Macro, MS Micro, MS Vitamins (MS hormone free) with 3 mg/l 2,4-Dichlorophenoxyacetic acid and 30 g/l maltose] to induce growth of cells. Plates are sealed with parafilm and incubated in the dark at 25° C. for 48 hours. The filter paper discs are then transferred to solidified selection media, LP3+100 mg/l hygromycin+250 mg/l cefotaxime and incubated in the dark at 25° C. After 2 weeks, the filter paper discs are transferred to solidified regeneration medium, MSK (Spangenberg et al 1995)+100 mg/l hygromycin+250 mg/l cefotaxime and incubated under direct light at 25° C. under fluorescent light conditions (16 hr light/8 hr dark photoperiod; 55 μmol $m^{-2}$ $sec^{-1}$) to encourage shoot and root development.

Hygromycin-resistant ($Hyg^r$) shoots with developed roots are then transferred to shoot elongation medium, MSO [MS Macro, MS Micro, MS Vitamins (MS hormone free) with 30 g/l maltose]+250 mg/l cefotaxime and incubated at 25° C. under an 8 h photoperiod until root systems become established. Finally, the plants are transferred to soil and maintained under containment glasshouse conditions.

G. Molecular Analysis of Transgenic Ryegrass Plants for Down-Regulation of Pollen Allergens Using Chimeric Genes Under Control of Pollen Specific Promoter Initial screening of the putative transgenic perennial ryegrass plants is achieved by PCR analysis.

The PCR-positive transgenic plants are then analysed by Southern hybridisation to show stable integration of the transgene. Genomic DNA is extracted from lyophilised plant material using a CTAB-based protocol. DNA samples (10-15 μg) are digested with BamHI, HindIII, EcoRI, or XhoI restriction enzymes. The resulting DNA fragments are separated on a 1% agarose gel and transferred to Hybond N (Amersham Pharmacia Biotech) membranes. Hybridisation is performed according to the manufacturer's instructions and incorporation of DIG-dUTP into DNA probes and detection of bound probes is performed using the DIG Luminescent Detection Kit (Roche Diagnostics Cat. No 1363514) following the supplier's protocol. Hybridisation conditions are: 4×SSC, 50% (v/v) formamide, 0.1% (w/v) N-lauroyl-sarcosine, 0.02% (w/v) SDS, and 2% (v/v) blocking solution at 42° C. Membranes are washed twice in 2×SSC/0.1% (w/v) SDS for five minutes at 25° C. then 0.2×SSC/0.1% (w/v) SDS followed by 0.1×SSC/0.1% (w/v) SDS, both for fifteen minutes at 68° C. Southern-positive plants are transferred to soil and grown under glasshouse conditions until flowering.

For SDS-polyacrylamide gel electrophoresis (SDS-PAGE) and western blot analysis, total proteins are extracted by grinding mature anthers from ryegrass plants in PBS buffer (10 mM phosphate buffer, pH 7.2; 150 mM NaCl) containing 1 mM PMSF followed by centrifugation at 14,000 rpm for 20 minutes at 4° C. Soluble proteins in the supernatant are quantified by Bio-Rad assay (Bio-Rad). Proteins are separated on SDS/15% PAGE gels on a Mini-Protean II system (Bio-Rad). The gels are either stained with Coomassie brilliant blue R250 or used in western blot analysis.

For western blotting, the proteins separated by SDS-PAGE are transferred onto nitrocellulose membrane. The blots are probed with primary antibodies or human sera overnight at 4° C. The primary antibodies, including polyclonal rabbit anti-Lol p 1 or polyclonal rabbit anti-Lol p 2, are diluted 1:1000 by using PBS. The sera of patients allergic to grass pollen are used at a dilution of 1:10. Binding of polyclonal antibodies is detected with goat anti-rabbit IgG conjugated to alkaline phosphatase (Bio-Rad) at a dilution of 1:1000, while binding of human sera is detected with mouse anti-human IgE antibodies conjugated to alkaline phosphatase (Southern Biotech) at a dilution of 1:1000. Secondary antibody detection is carried out for 2 hours at 25° C. The colour reaction is developed by using an alkaline phosphatase conjugate substrate kit (Bio-Rad). Equal loading of total proteins from samples of transgenic and non-transformed control plants for the western analysis is ensured by quantifying total protein content and Bio-Rad assay staining of replicate gels for each extraction.

EXAMPLE 6

The Generation of Transgenic Plants for Induction of Male Sterility and/or Transgene Containment Using Chimeric Genes Under Control of the Novel Pollen-Specific Promoter Transgenic male sterile plants are produced by introducing into the plant the nucleic acid molecule of the present invention in combination with a gene capable of modulating male fertility. Established methods for gene transfer to plants are used for the production of transgenic plants as described in 'Gene Transfer to Plants' I. Potrykus and G Spangenberg, Springer Lab Manual, 1995, ISBN 3-540 58406-4, and/or as set forth in Examples 3 and 5, above.

The gene used to modulate male fertility is a gene critical to pollen development and/or germination. Suitable genes include, for example, genes encoding pollen callose synthase, pollen tubulin, pollen actin or some other pollen-expressed 'house-keeping genes'. The chimeric genes transferred into the plant for induction of male sterility lead to decreased expression of the endogenous plant pollen-expressed gene, whether encoding pollen callose synthase, pollen tubulin, pollen actin or some other pollen-expressed 'house-keeping gene'. This is achieved by placing an anti-sense nucleic acid molecule or dsRNA or small interfering RNA (siRNA), derived from the plant pollen-expressed gene, operably under the control of the promoter according to the present invention.

A gene capable of modulating male fertility for the production of transgenic male sterile plants may also be a gene the expression of which results in cell death at the site of expression. Such genes include the gene encoding the bacterial secreted ribonuclease, barnase, derived from *Bacillus amyloliquefaciens*. The expression of a transferred chimeric gene that includes the coding sequence for the ribonuclease barnase from *Bacillus amyloliquefaciens*, operably under control of the nucleic acid molecule according to the present invention, leads to the specific-expression of the barnase gene in pollen, thereby reducing any unwanted side-effects of expression of barnase in other plant tissues.

EXAMPLE 7

The Restoration of Male Fertility in Male Sterile Transgenic Plants Using Chimeric Genes Under Control of the Novel Pollen-Specific Promoter for Hybrid Production Transgenic male fertile plants are produced by introducing into the plant the nucleic acid molecule of the present invention in combination with a gene capable of reverting the action of a gene that leads to male sterility. Established methods for gene transfer to plants are used for the production of transgenic plants as described in 'Gene Transfer to Plants' I. Potrykus and G Spangenberg, Springer Lab Manual, 1995, ISBN 3-540 58406-4, and/or as set forth in Examples 3 and 5, above.

The gene capable of restoring male fertility of transgenic male sterile plants—generated by the pollen-specific expression of a gene which results in cell death at the site of expression, including the gene encoding the bacterial secreted ribonuclease barnase from *Bacillus amyloliquefaciens*—is a gene that counteracts the effect of the male sterility gene. The barstar gene from *Bacillus amyloliquefaciens*, which encodes the inhibitor of the bacterial secreted ribonuclease barnase from *Bacillus amyloliquefaciens*, is used as male fertility restorer gene. Chimeric genes that include the barstar gene from *Bacillus amyloliquefaciens*, operably under control of the nucleic acid molecule according to the present invention, lead to the specific expression of the barstar gene in pollen. Crosses of transgenic male sterile plants expressing the barnase gene operably under control of a pollen-specific promoter, including the nucleic acid molecule according to the present invention, are made with pollen from transgenic male fertile plants expressing the barstar gene operably under control of the nucleic acid molecule according to the present invention. Offspring recovered from these crosses lead to fertile hybrid plants.

Those skilled in the art will appreciate that the invention described above is susceptible to variations and modifications other than those specifically described. It is to be understood that the invention includes all such variations and modifications. The invention also includes all of the steps, features, compositions and products referred to or indicated in this specification, individually or collectively, and any and all combinations of two or more of said steps or features.

Reference to any prior art in the specification is not, and should not be taken as, an acknowledgement or any form of suggestion that this prior art forms part of the common general knowledge in Australia or any other jurisdiction.

REFERENCES

Caplan, N. et al (2000); Gene 252:95-105

Fire, A. et al (1998); Nature 391:806-811

Hamilton D A, Roy M, Rueda J, Sindhu R K, Sanford J, Mascarenhas J P (1992) Dissection of a pollen-specific promoter from maize by transient transformation assays. *Plant Mol. Biol.* 18:211-218.

Jauhar P P (1993) Cytogenetics of the *Festuca-Lolium* complex. Relevance to breeding. In: Frankel R, Grossman M, Linskens H F, Maliga P, Riley R (eds) Monographs on theoretical and applied genetics, vol 18. Springer, Berlin Heidelberg New York, 243 pp.

Jefferson R A, Kavanagh T A, Bevan M W (1987) GUS fusions: β-glucuronidase as a sensitive and versatile gene fusion marker in higher plants, *EMBO J.* 6:3901-3907.

Potrykus I, Spangenberg G (eds.) (1995) Gene transfer to plants, Laboratory Manual, Springer Verlag, Heidelberg Sambrook J, Fritsch E F, Maniatis T (1989) Molecular cloning—a Laboratory Manual, Second Edition, Cold Spring Harbor Laboratory Press, New York, 1989.

Siegel M R, Latch G C M, Johnson M C (1985) *Acremonium fungal* endophytes of tall fescue and perennial ryegrass: significance and control. *Plant. Dis.,* 69: 179-183.

Spangenberg G, Wang Z Y, Potrykus I (1998) Isolation, culture and plant regeneration from protoplasts, In Cell Biology: A Laboratory Handbook, Second Edition, Vol 1, Academic Press Spangenberg G, Wang Z Y, Wu X, Nagel J, Potrukus I (1995), Transgenic perennial ryegrass (*Lolium perenne*) plants from microprojectile bombardment of embryogenic suspension cells, Plant Science 108:209-217

The invention claimed is:

1. An isolated nucleic acid molecule comprising a sequence of nucleotides selected from the group consisting of
   (a) the nucleotide sequence set forth in SEQ ID NO: 2 or 3;
   (b) a nucleotide sequence at least 100 nucleotides in length which is a fragment of (a) NO: 3 wherein said molecule drives pollen-specific expression.

2. The isolated nucleic acid molecule according to claim 1 wherein said molecule drives pollen-specific expression of an operably-linked second nucleic acid molecule.

3. The isolated nucleic acid molecule according to claim 2 wherein said second nucleic acid molecule is capable of down-regulating expression of a pollen alergen.

4. The isolated nucleic acid molecule according to claim 3 wherein said pollen allergen is Lol p 1 and/or Lol p 2.

5. A vector comprising the nucleic acid molecule according to claim 1.

6. The vector according to claim 5, further comprising a second nucleic acid molecule and a terminator, said nucleic acid molecule, second nucleic acid molecule, and terminator being operably linked so as to result in expression of said second nucleic acid molecule.

7. The vector according to claim 6 wherein said second nucleic acid molecule is capable of modifying expression of a pollen allergen.

8. The vector according to claim 7 wherein said pollen allergen is Lol p 1 and/or Lol p 2.

9. A plant cell, plant, plant seed or other plant part comprising the nucleic acid molecule according to claim 1 or the vector according to claim 5.

10. A method of modifying gene expression in pollen, said method comprising
    (a) introducing into a plant cell an effective amount of the nucleic acid molecule according to claim 1, or the vector according to claim 5, and
    (b) directing pollen-specific expression of an operably-linked second nucleic acid molecule
    (c) selecting a transformed plant cell containing said nucleic acid;
    wherein said nucleic acid modifies gene expression in pollen.

11. A method of producing a plant with reduced male fertility compared with a wild-type plant, said method including
    (a) introducing into the plant the nucleic acid molecule according to claim 1 operably linked to a second nucleic acid molecule that modulates male fertility, and
    (b) selecting a transformed plant with reduced male fertility compared with a wild-type plant.

12. The method according to claim 11 wherein said second nucleic acid molecule modulates pollen development.

13. The method according to claim 12 wherein said second nucleic acid molecule encodes bacterial ribonuclease barnase.

14. A plant produced by the method according to claim 11.

15. The plant according to claim 14 wherein said plant is a male sterile plant.

16. A preparation for transforming a plant comprising the nucleic acid molecule according to claim 1.

17. An isolated nucleic acid molecule capable of modifying pollen-specific expression, comprising a nucleotide sequence selected from the group consisting of the sequences set forth in SEQ ID NO:2 and SEQ ID NO:3.

18. The isolated nucleic acid molecule according to claim 1 comprising a sequence of nucleotides selected from the group consisting of:
(a) the nucleotide sequence set forth in SEQ ID NO: 3:
(b) a nucleotide sequence at least 100 nucleotides in length which is a fragment of (a) wherein said molecule drives pollen-specific expression.

19. The isolated nucleic acid molecule according to claim 1 comprising a sequence of nucleotides selected from the group consisting of:

(a) the nucleotide sequence set forth in SEQ ID NO: 2:
(b) a nucleotide sequence at least 100 nucleotides in length which is a fragment of (a) wherein said molecule drives pollen-specific expression.

20. The isolated nucleic acid molecule according to claim 17 comprising the nucleotide sequence set forth in SEQ ID NO: 3.

21. The isolated nucleic acid molecule according to claim 17 comprising the nucleotide sequence set forth in SEQ ID NO: 2.

* * * * *

UNITED STATES PATENT AND TRADEMARK OFFICE
CERTIFICATE OF CORRECTION

PATENT NO. : 7,355,096 B2  Page 1 of 1
APPLICATION NO. : 10/561283
DATED : April 8, 2008
INVENTOR(S) : G. Spangenberg et al.

It is certified that error appears in the above-identified patent and that said Letters Patent is hereby corrected as shown below:

| COLUMN | LINE | ERROR |
|---|---|---|
| 25 (Claim 1, | 38 line 3) | "the group consisting of" should read --the group consisting of:-- |
| 25 (Claim 1, | 40 line 5) | "or 3;" should read --or 3; and-- |
| 25 (Claim 3, | 49 line 3) | "alergen." should read --allergen.-- |
| 26 (Claim 10, | 36 line 2) | "method comprising" should read --method comprising:-- |
| 26 (Claim 10, | 39 line 5) | "according to claim 5, and" should read --according to claim 5; and-- |
| 27 (Claim 18, | 6 line 4) | "SEQ ID NO: 3:" should read --SEQ ID NO: 3; and-- |

Signed and Sealed this

Eighteenth Day of November, 2008

JON W. DUDAS
*Director of the United States Patent and Trademark Office*

SEQUENCE LISTING

<160> NUMBER OF SEQ ID NOS: 10

<210> SEQ ID NO 1
<211> LENGTH: 3356

-continued

```
<212> TYPE: DNA
<213> ORGANISM: Lolium perenne
<220> FEATURE:
<221> NAME/KEY: misc_feature
<222> LOCATION: (3324)..(3324)
<223> OTHER INFORMATION: n is a, c, g, or t
<220> FEATURE:
<221> NAME/KEY: misc_feature
<222> LOCATION: (3328)..(3328)
<223> OTHER INFORMATION: n is a, c, g, or t
<220> FEATURE:
<221> NAME/KEY: misc_feature
<222> LOCATION: (3333)..(3333)
<223> OTHER INFORMATION: n is a, c, g, or t
<220> FEATURE:
<221> NAME/KEY: misc_feature
<222> LOCATION: (3346)..(3346)
<223> OTHER INFORMATION: n is a, c, g, or t

<400> SEQUENCE: 1
agtgtaacct aggactctag gccagatcgt gacattggaa tagtgcacga catttccctg      60
catacgtaac gcctatgggt atggagcttc ataccgagac tcccaagtat cataccagag     120
gggacgtggc ctcctctatt ctaggggcga cgccacccct ggcaataaaa ataggaactt     180
ctactagata agggggaggg ctcgaagcaa caaagaggct aagaaaggcg aaaatcaagc     240
aagaacacaa acccaacaag ccagagctaa acaagcctta gcaccatggt ctctcgcact     300
cgaaaataac gaggcgagat gacactcttt ccattccaac atttcatagc ttagtagcta     360
cccaagagga ggaacaagca ccagccaact tcccgccgga agcggcaccc actcagactc     420 actagcaccct cgcgcacaat caataaaaac accaccacca agaagtaggg ttgttattga     480
cgatgtattc tcggtcccta aattgtatat ctctcgtgtg catgtggatg ttacccaatg     540
gaatcgtggt cacaagccca ccacctacat aagaatatac aaccgggaac caaaaccctg     600
acactaggca aatcattagg gccacgccga ctatctcatt cccgcacgcg tctaggtttc     660
ccgcccgttt ctaccccttg tgggtatccc ccatcattct tgtttgtatt ggtccaaaaa     720
atcagcaaag tttgctttgc cgtgtgtatt catataacac tcgataatga ccccatcggc     780
cttatttttt tattgtttcc ttcctgcctt ttcttcccg cgatctttca gcccttgtgt      840
ccctatatat acccatctct cggatacata attcacaacc cacctccacc ataaagtaca     900
aagaagagca ttcactctag gaaccttga aggtgtgggt cttgtataaa gtcatggcag      960
cgatgtacaa ggcttgcatc atctagggtt cctagatgaa acgcttagca tcagctaggt    1020
aataataacc ttgggtgaca tagttgccaa aacaagctta tattgtgcac atgtgcgtgt    1080
gtcatgggac tggaaagggt cgccggtgtg aaccactgat gtgtgctgcc atttaggaag    1140
actctagatg aatgggggaa ctcccaggtc gggtccacca gaggaaaatc ttgcgagatc    1200
ttgggctgaa tcattgaatt tcatgtacca agtaactaac caaatagaaa ccaagagaaa    1260
atctcattgt tcagcagtct ttcgttgaat tttagaggga tatgcggtgg agggcctccg    1320
aggcagcgtt tcgccgcata ccacatttcg gagggccgaa atccatccaa aactatcaag    1380
tgggactaac acatgaacat acgtgtgttg agattctgag atgcccaaga gccagctccc    1440
gcgcgtgacc cacttcaccg gcgaccgctg ccacttagga aggttcttga ctgaaaaagg    1500
gaaaactccc acgatgggtt cacccgagga atcttgcga gatcatgagc tcaaccattg    1560 cttttccatgt tcctatgaac taaccaaaca atcaagtgaa atcccattg gccaccggta    1620 gtttaaataa tttcagaagc gtagaccatg cttcggatgg ccaaaatcca cctaaaactt    1680
gcaagtgggc ctaatatgtg tgtaaaagtg tgctgggatg gtgaggggggc caagagctag    1740
```

-continued

```
ctagcgtggc ggcatgctgt cgtgggagta agaaaatctc tgcacagtgt gttttagggc    1800
aacacttggc aaatgtgtga tcttcggaac atcccaagct tgggaccgtc aagttgcttt    1860
tgtgcgcaaa gtaaacgcaa aaaacatgcg ccactccttt accatatgcc ggacaaaaaa    1920
aacttggcaa atggttattt ccttggtgat cggtgttctg cgccgtatgc cgatggtcga    1980
cataggcttt gccgtgttct gcgttgcctt tgtcgtggct ttttcccaca tggcaaatcc    2040
ataatttcca gtagtgactc aataatattt gaaggcaaga acaccaggga gccgaattga    2100
atttccggca tatccgctac tatagattga aaataaggag gcggatcatc tccttggtgc    2160 aaccccttt  ttgtctaaaa ataattttct ttttgaatat tttacatttc ttcatactat    2220
aattttggat acataaaata ttaactttat atgaaaat  ataattccaa tacttttgca    2280
ctcatcaaat aattaatttt ggatatataa ctagttgagt tgtttatgca aaattcctat    2340
taaattattt tcggtaccaa acaatgtaaa attagtaagg tcataactag ttgtgcaacg    2400
tatactgaaa aaattaattt tggaatttcg caaaaaaaaa aatggataca tggaacgctc    2460
aggcgatgtc tgtggccatg aaaccgcgct tgtcctgtgc ataattctag ggtgtgggtg    2520
cttctataaa tggataatga gcatgcatca gaacgctcca gcgatgtttg tggccatgag    2580
acagagcttg tccgtgcatg cctacgcggc tctccctcgc cgtggcccaa gctctgttcc    2640
cttccgacag acccggccgg tacaagcgcc tgcgacatgg ccgaagcgcc gcccatccgc    2700
gcataaatac ccgcacacca tctatcaccg attcacaacc aacagcagca gcacacatat    2760
acacacaaga accatccaac aaatccagaa tggcttcctc atcaagcagg atgctggcgg    2820
cggcggcgct ggcggcgctg ttcgtgggcg cgatgtgcga ggccccgtg  acgttcacgg    2880 tagagaaggg ctccgacgag aagaacctgg cgctgtcgat caagtacaac aaggagggcg    2940
actccatggc ggaggtggag ctcaaggagc acggctccaa cgagtggctg gccctgaaga    3000
agaacggcga cggcgtgtgg gagatcaaga gcgacaagcc gctcaagggg ccattcaact    3060
tccgcttcgt gtccgagaag gggatgagga acgtgttcga cgacgtggtt ccggcggagt    3120
tcaaggtcgg caccacctac aagcccgagg agtagatccg ccatcggtcg tcatcggaag    3180
ttttcgattt tcctcatatc atgaataatt tgtcgaggtt tttgtcagtg aggtggtgat    3240
tgggagaagc acaactatgg atgtgcttcc tagtatctcc catgcaccca ttaccatgac    3300 caatatttt  ttatatgaat cggnttangt aanttaattt aaaagnccct taaaag        3356
```

<210> SEQ ID NO 2  
<211> LENGTH: 2789  
<212> TYPE: DNA  
<213> ORGANISM: Lolium perenne

<400> SEQUENCE: 2

```
agtgtaacct aggactctag gccagatcgt gacattggaa tagtgcacga catttccctg      60
catacgtaac gcctatgggt atggagcttc ataccgagac tcccaagtat cataccagag    120
gggacgtggc ctcctctatt ctaggggcga cgccacccct ggcaataaaa ataggaactt    180
ctactagata aggggaggg  ctcgaagcaa caaagaggcg aagaaaggcg aaaatcaagc    240
aagaacacaa acccaacaag ccagagctaa acaagcctta gcaccatggt ctctcgcact    300
cgaaaataac gaggcgagat gacactcttt ccattccaac atttcatagc ttagtagcta    360
cccaagagga ggaacaagca ccagccaact tcccgccgga agcggcaccc actcagactc    420
actagcacct cgcgcacaat caataaaaac accaccacca agaagtaggg ttgttattga    480
cgatgtattc tcggtcccta aattgtatat ctctcgtgtg catgtggatg ttacccaatg    540
```

-continued

```
gaatcgtggt cacaagccca ccacctacat aagaatatac aaccgggaac caaaaccctg    600
acactaggca aatcattagg gccacgccga ctatctcatt cccgcacgcg tctaggtttc    660
ccgcccgttt ctaccccttg tgggtatccc ccatcattct tgtttgtatt ggtccaaaaa    720
atcagcaaag tttgctttgc cgtgtgtatt catataacac tcgataatga ccccatcggc    780 cttattttt tattgtttcc ttcctgcctt ttcttcccg cgatctttca gcccttgtgt      840
ccctatatat acccatctct cggatacata attcacaacc cacctccacc ataaagtaca    900
aagaagagca ttcactctag gaaccttga aggtgtgggt cttgtataaa gtcatggcag     960
cgatgtacaa ggcttgcatc atctagggtt cctagatgaa acgcttagca tcagctaggt   1020
aataataacc ttgggtgaca tagttgccaa aacaagctta tattgtgcac atgtgcgtgt   1080
gtcatgggac tggaaagggt cgccggtgtg aaccactgat gtgtgctgcc atttaggaag   1140
actctagatg aatgggggaa ctcccaggtc gggtccacca gaggaaaatc ttgcgagatc   1200
ttgggctgaa tcattgaatt tcatgtacca agtaactaac caaatagaaa ccaagagaaa   1260
atctcattgt tcagcagtct ttcgttgaat tttagaggga tatgcggtgg agggcctccg   1320
aggcagcgtt tcgccgcata ccacatttcg gagggccgaa atccatccaa aactatcaag   1380
tgggactaac acatgaacat acgtgtgttg agattctgag atgcccaaga gccagctccc   1440
gcgcgtgacc cacttcaccg cgaccgctgc ccacttagga aggttcttga ctgaaaaagg   1500
gaaaactccc acgatgggtt cacccgagga atcttgcga gatcatgagc tcaaccattg    1560
ctttccatgt tcctatgaac taaccaaaca atcaagtgaa atcccattg ccaccggta     1620 gtttaaataa tttcagaagc gtagaccatg cttcggatgg ccaaaatcca cctaaaactt   1680
gcaagtgggc ctaatatgtg tgtaaaagtg tgctgggatg gtgaggggc caagagctag    1740 ctagcgtggc ggcatgctgt cgtgggagta agaaaatctc tgcacagtgt gttttagggc   1800
aacacttggc aaatgtgtga tcttcggaac atcccaagct tgggaccgtc aagttgcttt   1860
tgtgcgcaaa gtaaacgcaa aaaacatgcg ccactccttt accatatgcc ggacaaaaaa   1920
aacttggcaa atggttattt ccttggtgat cggtgttctg cgccgtatgc cgatggtcga   1980
cataggcttt gccgtgttct gcgttgcctt tgtcgtggct ttttcccaca tggcaaatcc   2040
ataatttcca gtagtgactc aataatattt gaaggcaaga acaccaggga gccgaattga   2100
atttccggca tatccgctac tatagattga aaataaggag gcggatcatc tccttggtgc   2160
aacccctttt ttgtctaaaa ataatttct ttttgaatat tttacatttc ttcatactat    2220
aattttggat acataaaata ttaactttat atatgaaaat ataattccaa tacttttgca   2280
ctcatcaaat aattaatttt ggatatataa ctagttgagt tgtttatgca aaattcctat   2340
taaattattt tcggtaccaa acaatgtaaa attagtaagg tcataactag ttgtgcaacg   2400
tatactgaaa aaattaattt tggaatttcg caaaaaaaa aatggataca tggaacgctc    2460
aggcgatgtc tgtggccatg aaaccgcgct tgtcctgtgc ataattctag ggtgtgggtg   2520
cttctataaa tggataatga gcatgcatca gaacgctcca gcgatgtttg tggccatgag   2580
acagagcttg tccgtgcatg cctacgcggc tctccctcgc cgtggcccaa gctctgttcc   2640
cttccgacag acccggccgg tacaagcgcc tgcgacatgg ccgaagcgcc gcccatccgc   2700
gcataaatac ccgcacacca tctatcaccg attcacaacc aacagcagca gcacacatat   2760
acacacaaga accatccaac aaatccaga                                      2789
```

<210> SEQ ID NO 3

```
<211> LENGTH: 953
<212> TYPE: DNA
<213> ORGANISM: Lolium perenne

<400> SEQUENCE: 3
agcttgggac cgtcaagttg cttttgtgcg caaagtaaac gcaaaaaaca tgcgccactc      60
ctttaccata tgccggacaa aaaaaacttg gcaaatggtt atttccttgg tgatcggtgt     120
tctgcgccgt atgccgatgg tcgacatagg ctttgccgtg ttctgcgttg cctttgtcgt     180 ggcttttcc cacatggcaa atccataatt ccagtagtg actcaataat atttgaaggc       240
aagaacacca gggagccgaa ttgaatttcc ggcatatccg ctactataga ttgaaaataa     300
ggaggcggat catctccttg gtgcaacccc ttttttgtct aaaaataatt ttcttttttga    360 atattttaca tttcttcata ctataatttt ggatacataa aatattaact ttatatatga    420
aaatataatt ccaatacttt tgcactcatc aaataattaa ttttggatat ataactagtt    480
gagttgttta tgcaaaattc ctattaaatt attttcggta ccaaacaatg taaaattagt    540
aaggtcataa ctagttgtgc aacgtatact gaaaaaatta attttggaat ttcgcaaaaa    600
aaaaaatgga tacatggaac gctcaggcga tgtctgtggc catgaaaccg cgcttgtcct    660
gtgcataatt ctagggtgtg ggtgcttcta taaatggata atgagcatgc atcagaacgc    720
tccagcgatg tttgtggcca tgagacagag cttgtccgtg catgcctacg cggctctccc    780
tcgccgtggc ccaagctctg ttcccttccg acagacccgg ccggtacaag cgcctgcgac    840
atggccgaag cgccgcccat ccgcgcataa atacccgcac accatctatc accgattcac    900
aaccaacagc agcagcacac atatacacac aagaaccatc caacaaatcc aga           953

<210> SEQ ID NO 4
<211> LENGTH: 6
<212> TYPE: DNA
<213> ORGANISM: Zea mays

<400> SEQUENCE: 4 aggtca                                                                   6

<210> SEQ ID NO 5
<211> LENGTH: 12
<212> TYPE: DNA
<213> ORGANISM: Lycopersicon esculentum

<400> SEQUENCE: 5
tgtggttata ta                                                           12

<210> SEQ ID NO 6
<211> LENGTH: 4
<212> TYPE: DNA
<213> ORGANISM: Nicotiana tabacum

<400> SEQUENCE: 6 gtga                                                                     4

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
aaaagtgtgc tgggatggtg                                                   20
```

```
<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
ccatccaaca aatccagaat ggcttcc                                              27

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
ctttaactat gccgggatcc atcg                                                 24

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
taaccttcac ccggttgcca gagg                                                 24
```